(12) United States Patent
Fujita et al.

(10) Patent No.: US 7,424,819 B2
(45) Date of Patent: Sep. 16, 2008

(54) GAS SENSOR

(75) Inventors: Yasuhiro Fujita, Gifu (JP); Masataka Taguchi, Aichi (JP); Daisuke Miyata, Nagoya (JP); Tetsuma Shimozato, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/783,807

(22) Filed: Apr. 12, 2007

(65) Prior Publication Data
US 2007/0243760 A1    Oct. 18, 2007

(30) Foreign Application Priority Data
Apr. 13, 2006    (JP)    .............................. 2006-111138

(51) Int. Cl.
*G01N 9/00*    (2006.01)
(52) U.S. Cl. ..................... 73/31.05; 204/424
(58) Field of Classification Search ............... 73/23.31, 73/31.05; 204/424, 426, 431; 29/595
See application file for complete search history.

(56) References Cited

U.S. PATENT DOCUMENTS

| | | | | |
|---|---|---|---|---|
| 4,507,191 | A * | 3/1985 | Ebizawa et al. ............. | 204/427 |
| 4,923,587 | A * | 5/1990 | Nishio et al. ................ | 204/424 |
| 5,049,255 | A * | 9/1991 | Wolfe et al. ................. | 204/428 |
| 5,573,650 | A * | 11/1996 | Fukaya et al. ............... | 204/424 |
| 5,679,226 | A * | 10/1997 | Furusaki et al. ............. | 204/424 |
| 5,759,365 | A * | 6/1998 | Yamada et al. .............. | 204/424 |
| 6,267,857 | B1 * | 7/2001 | Akatsuka et al. ............ | 204/424 |
| 6,383,353 | B1 * | 5/2002 | Akatsuka et al. ............ | 204/424 |
| 6,477,887 | B1 * | 11/2002 | Ozawa et al. ............... | 73/31.05 |
| 6,660,143 | B1 * | 12/2003 | Akatsuka et al. ............ | 204/424 |
| 6,688,157 | B2 * | 2/2004 | Yamada et al. .............. | 73/23.2 |
| 6,851,180 | B2 * | 2/2005 | Hattori et al. ................. | 29/619 |
| 6,866,517 | B2 * | 3/2005 | Kimata et al. ................. | 439/33 |
| 7,032,433 | B2 * | 4/2006 | Hayashi et al. ............. | 73/31.05 |
| 7,228,621 | B2 * | 6/2007 | Hattori et al. ................. | 29/758 |
| 7,340,942 | B2 * | 3/2008 | Matsuo et al. ............. | 73/31.05 |
| 2005/0040039 | A1 * | 2/2005 | Kojima et al. ............... | 204/424 |
| 2006/0288759 | A1 * | 12/2006 | Okumura et al. ........... | 73/31.05 |

FOREIGN PATENT DOCUMENTS

JP    2004093501 A    *    3/2004
WO    WO 2004010130 A1    *    1/2004

* cited by examiner

*Primary Examiner*—Hezron E. Williams
*Assistant Examiner*—John Fitzgerald
(74) *Attorney, Agent, or Firm*—Sughrue Mion, PLLC

(57) ABSTRACT

A gas sensor in which respective terminal leads are fitted and connected to respective electrodes on inner and outer circumferential surface of a hollow, cup-shaped detection element When a leading end connecting portion of a terminal lead (71, 91) is disposed on the front end side of a separator (111) and an intermediate portion (74, 94) extending from the rear end of the leading end connecting portion is inserted into a hole (113), a spring tab (77, 97) provided on the intermediate portion (74, 94) is pressed against a second wall surface (117) of the hole (113), whereby an engagement portion (76, 96) is pressed against a first wall surface opposite the second wall surface (117). The first projection (118) is formed on the first wall surface of the hole (113) so that it can come into contact with and support a first face (76*b*, 96*b*) of the engagement portion (76, 96) on opposing lateral sides of the spring tab (77, 97).

5 Claims, 14 Drawing Sheets

GAS SENSOR

BACKGROUND OF THE INVENTION

1. Field of the Invention

The present invention relates to a gas sensor (hereinafter also referred to as a "sensor") such as an oxygen sensor for detecting the concentration of oxygen in a gas to be measured, such as exhaust gas discharged from, for example, an internal combustion engine.

2. Description of the Related Art

Patent Document 1 discloses a typical example of such a gas sensor, which has the structure shown in FIG. 11. This oxygen sensor 1 is composed of a detection element (hereinafter also referred to as an "element") 21, a metal housing 11, etc. The detection element 21 is formed from a cup-shaped (tubular) solid electrolyte having an inner electrode (layer) and an outer electrode (layer) formed on inner and outer surfaces thereof, respectively, and a closed front end (lower end in FIG. 11). The metal housing 11 holds the detection element 21 therein, and the oxygen sensor 1 is mounted to an exhaust gas pipe of the internal combustion engine via the metal housing 11. The inner electrode (reference electrode) on the inner circumferential surface (inner wall surface) of the detection element 21 is exposed to a reference gas (ambient atmosphere), and the outer electrode (measurement electrode) on the outer circumferential surface (outer wall surface) of the detection element 21 is exposed to an exhaust gas. In this manner, an electromotive force is generated between the two electrodes in accordance with a difference in oxygen concentration between the inner and outer surfaces of the detection element 21. A signal induced by this electromotive force is output to a control circuit, and is used to detect the concentration of oxygen in the exhaust gas and control the air-fuel ratio.

In the sensor 1 shown in FIG. 11, terminal leads 71 and 91 are connected to the inner and outer electrodes (hereinafter also referred to as "electrodes") formed on the inner and outer circumferential surfaces of the detection element 21; and lead wires 41 for signal output are connected to the rear ends (upper ends in FIG. 11) of the terminal leads 71 and 91. Of these terminal leads 71 and 91, the terminal lead (output terminal) 71 connected to the electrode formed on the inner circumferential surface of a rear end portion of the detection element 21 has a leading end connecting portion 73, as shown in FIG. 2A. This leading end connecting portion 73 is a cylindrical portion (a tubular portion having a C-shaped or Landolt-ring-shaped transverse cross section) which is formed by, for example, bending a metal plate and which has a slit-like opening M along the generating line. The leading end connecting portion 73 is brought into press contact with and is connected to the inner electrode by means of press-fitting the leading end connecting portion 73 into the interior of the detection element 21 from the rear end thereof. As shown in FIG. 3A, the terminal lead (ground terminal) 91 connected to the electrode formed on the outer circumferential surface of the element 21 has a leading end connecting portion 93 at its front end portion. This leading end connecting portion 93 is a cylindrical portion which is formed by, for example, bending a metal plate and which has a slit-like opening M along the generating line. The leading end connecting portion 93 is brought into press contact with and is connected to the outer electrode by means of press-fitting the leading end connecting portion 93 onto the outer circumference of the detection element 21 from the rear end thereof. These terminal leads 71 and 91 include trailing end connecting portions 75 and 95 and intermediate portions 74 and 94, respectively. The trailing end connecting portions 75 and 95 are connected to respective distal ends of the lead wires 41 by means of crimping. The intermediate portions 74 and 94 connect the cylindrical leading end connecting portions 73 and 93 and the trailing end connecting portions 75 and 95, respectively. The terminal leads 71 and 91 are configured such that after being press-fitted into and onto the detection element 21, respectively, the leading end connecting portions 73 and 93 are pressed against the inner and outer electrodes of the detection element 21 by means of their spring forces, to thereby electrically connect thereto.

Assembly of the sensor 1, involving such electrical connection, has been performed as follows. An element-side subassembly (main-body-side assembly) 201 in which the element 21 is fixedly disposed inside the metal housing 11 assuming a tubular shape by use of a seal member 53 or the like as shown on the left side of FIG. 12 is assembled along with a terminal-lead-side subassembly 301 in which the terminal leads 71 and 91 are connected to the distal ends of the lead wires 41 within a tubular protection sleeve 31 (in the form of a stepped cylindrical tube) as shown on the right side of FIG. 12. The terminal leads 71 and 91 of the terminal-lead-side subassembly 301 are inserted into a plurality of insertion holes 113 provided in a cylindrical-columnar separator 111 formed of an insulating material and extending through the separator in the front-rear direction. This structure secures electrical insulation between the terminal leads 71 and 91 and between the terminal leads 71 and 91 and the protection sleeve 31, serving as a casing. FIG. 13 is a view of the separator 111 of the terminal-lead-side subassembly 301 on the right side of FIG. 12, as viewed from the side where the front end (lower end in FIG. 12) thereof is located. As shown in FIG. 13, the tubular leading end connecting portions 73 and 93 are disposed so that their centers coincide with the center of a front end surface 112 of the separator 111 or are located in the vicinity of the center. At the front end of the separator 111, the leading end connecting portions 73 and 93 form a so-called double circle. Notably, in FIG. 12, a pole-shaped heater 61 extending along an axis G is provided below the terminal-lead-side subassembly 301 and held within the leading end connecting portion 73 of the terminal lead 71 to project from the leading end connecting portion 73. However, the heater 61 will not be described here.

The sensor 1 is assembled as follows. After the centers (axis G) of the leading end connecting portions 73 and 93 of the terminal leads 71 and 91 of the terminal-lead-side subassembly 301 are made exactly or generally coincident with the axis G of the element 21 of the element-side subassembly 201 as shown in FIG. 12, these subassemblies are axially moved toward each other. Thus, the leading end connecting portions 73 and 93 of the terminal leads 71 and 91 are simultaneously fitted onto the inner and outer circumferences of the rear end 25 of the detection element 21. Notably, in order to facilitate this fitting, chamfers 26 and 27 are formed at respective corners between the rear end 25 of the element 21 and the inner and outer circumferential surfaces thereof. Meanwhile, a taper portion 84 and outwardly-expanded teeth 98 are provided at the front ends of the leading end connecting portions 73 and 93 of the terminal leads 71 and 91 so as to serve as guides. Simultaneously with fitting of these leading end connecting portions, a front end portion of the protection sleeve 31 is fitted onto a rear-end side thick cylindrical portion 17 of the metal housing 11.

The terminal-lead-side subassembly 301 used for assembly of such a sensor is generally assembled through the following steps. The distal end portions of the lead wires 41 are passed through a seal member 131 and then through the insertion holes 113 of the separator 111, and the trailing end connecting portions (connector portions) 75 and 95 at the rear ends of the terminal leads 71 and 91 are connected to the distal ends of the passed lead wires 41 by means of crimping. Subsequently, rear end (proximal end) portions of the lead wires 41 are pulled toward the rear of the separator 111 and the seal member 131 (upward in FIG. 12) until the leading end connecting portions 73 and 93 of the terminal leads 71 and 91 engage the front end surface 112 of the separator 111, whereby positioning of the terminal leads 71 and 91 is completed.

Meanwhile, in the course of assembling the terminal-lead-side subassembly 301, the tubular leading end connecting portions 73 and 93 of the terminal leads 71 and 91 must be positioned, with a predetermined accuracy, at predetermined positions corresponding to the rear end of the element 21 of the element-side subassembly 201 on the front end surface 112 of the separator 111. If the leading end connecting portions 73 and 93 are not positioned in such a manner, the leading end connecting portions 73 and 93 cannot be smoothly fitted onto the inner and outer circumferential surfaces of the rear end 25 of the element 21 at the time of assembling the subassemblies 201 and 301 toward each other. Conventionally, the element-side subassembly 201 has been relatively easily assembled as designed. However, in assembling the terminal-lead-side subassembly 301, it has been difficult to accurately position the tubular leading end connecting portions 73 and 93 of the terminal leads 71 and 91 at designated positions on the front end surface 112 of the separator 111. This is because the intermediate portions 74 and 94 of the terminal leads 71 and 91 allow for a so-called swaying motion; i.e., sway in the insertion holes 113 of the separator 111.

Therefore, in the above-mentioned sensor described in Patent Document 1, the terminal leads 71 and 91 and the insertion holes 113 of the separator 111 into which the terminal leads 71 and 91 are inserted are configured to have the following relation. In order to stably position the terminal leads 71 and 91 within the insertion holes 113 of the separator 111, as shown in FIGS. 2 and 3, engagement portions 76 and 96 extending in the front-rear direction are respectively formed at the intermediate portions 74 and 94 between the leading end connecting portions 73 and 93 and the trailing end connecting portions 75 and 95 of the terminal leads 71 and 91, and spring tabs 77 and 97 are centrally formed in the engagement portions 76 and 96. The spring tabs 77 and 97 are formed through punching and bending so as to project from second faces 76a and 96a of the engagement portions 76 and 96 and have end portions 77a and 97a. By virtue of this configuration, when the intermediate portions 74 and 94 of the terminal leads 71 and 91 are inserted into the insertion holes 113, as shown in FIGS. 12 and 14, the spring tabs 77 and 97 are pressed against the wall surfaces of the holes 113 by means of spring force, while pressing the engagement portions 76 and 96 against the opposite wall surfaces of the holes 113. Such pressing prevents the intermediate portions 74 and 94 from swaying within the holes 113.

As shown in, for example, FIG. 3-b of Patent Document 1, the insertion holes 113 of the separator 111 are formed at predetermined positions around the axis to pass through the separator in the front-rear direction. However, each hole (the lead-wire insertion hole 31a in FIG. 3-b of Patent Document 1) has a generally triangular transverse cross section which extends toward the axis G to form an apex. Therefore, in the above-described sway prevention means, as shown in FIG. 14, the spring tabs 77 and 97 are pressed against the wall surfaces of the holes 113 remote from the axis G, and the first faces 76b and 96b of the engagement portions 76 and 96 are pressed, at their opposite lateral edge corners 76c and 96c, against the opposite wall surfaces of the holes 113. That is, the terminal leads 71 and 91 are positioned within the insertion holes 113 in this manner, and the leading end connecting portions 73 and 93 at their front ends are positioned on the front end surface 112 of the separator 111 as shown in FIG. 13.

[Patent Document 1] Japanese Patent Application Laid-Open (kokai) No. 2004-53425

3. Problems to be Solved by the Invention

The above-described means for preventing swaying of the terminal leads 71 and 91 raises the following problem. In the course of assembling the terminal-lead-side subassembly 301, the terminal leads 71 and 91 are inserted into the insertion holes 113 of the separator 111, and the leading end connecting portions 73 and 93 at their front ends are positioned and disposed on the front end surface 112 of the separator 111. However, this assembly operation cannot be carried out easily, or a large amount of labor (man-hours) is required for such positioning. That is, the dimensions of relevant portions of the holes 113 and the terminal leads 71 and 91 are set so that when the leading end connecting portions 73 and 93 engage the front end surface 112 of the separator 111, the centers of the leading end connecting portions 73 and 93 are located at a predetermined position on the front end surface 112. However, in assembling the terminal-lead-side subassembly 301, the desired positioning cannot be achieved by merely inserting the terminal leads 71 and 91 into the insertion holes 113 of the separator 111 and pulling out the lead wires 41 connected to the trailing end connecting portions 75 and 95 at the rear ends of the terminal leads 71 and 91 toward the proximal end side. Accordingly, during assembly of the terminal-lead-side subassembly 301, a worker has to actively adjust the positions of the leading end connecting portions 73 and 93 so that they are disposed at predetermined positions on the front end surface 112 of the separator 111.

Further, even when the leading end connecting portions 73 and 93 are correctly disposed at the desired positions during assembly, as shown in FIG. 15, the positions of the leading end connecting portions 73 and 93 may change due to various external forces, vibration, or the like, applied to the leading end connecting portions 73 and 93 before the two subassemblies are assembled together. Such a change in position occurs because, as viewed in a transverse cross section, both the intermediate portions 74 and 94 of the terminal leads 71 and 91 can easily move to rotate within the insertion holes 113 of the separator 111. Thus, the leading end connecting portions 73 and 93 move in a swinging fashion about the intermediate portions 74 and 94 when an external force or the like is applied thereto. The reason for this movement is that each insertion hole 113 of the separator 111 assumes a generally triangular shape in the transverse cross section as described above. That is, in the transverse cross section, each hole 113 has opposite inclined wall surfaces, the distance therebetween decreasing toward the axis G. Meanwhile, the opposite lateral edge corners 76c and 96c of the engagement portions 76 and 96 of the intermediate portions 74 and 94 are engaged with and supported by the inclined wall surfaces of the corresponding holes 113, and such support is unstable. In the case where such support is employed, when an external force is laterally applied to the leading end connecting portion 73 (93) about the intermediate portion 74 (94), the intermediate portion 74 (94) readily rotates within the corresponding hole 113. Even when the intermediate portion 74 (94) rotates by a small amount, the leading end connecting portion 73 (93) at the front end swings a great distance in the transverse cross section, and its position changes considerably.

The above-described change in position may cause an assembly related problem in that when the terminal-lead-side subassembly 301 and the element-side subassembly 201 are assembled together, the leading end connecting portions 73 and 93 of the terminal leads 71 and 91 collide with the rear end portion of the detection element 21, and cannot be fitted smoothly. In such a case, the cylindrical portions, which constitute the leading end connecting portions 73 and 93, deform (for example, are crushed), chipping occurs at the rear end portion of the detection element 21, or fitting failure (connection failure) occurs, whereby the production yield of the sensor decreases.

SUMMARY OF THE INVENTION

The present invention has been accomplished in view of the above-described problems relating to assembly of a sensor, and an object thereof is to enable leading end connecting portions of the terminal leads to be easily positioned at desired positions in relation to a front end surface of the separator when terminal leads are inserted into the holes of a separator, and to reduce the possibility of a change in such positioning. In this manner, the leading end connecting portions of the terminal leads may be smoothly fitted to a rear end portion of a detection element in the course of assembling an element-side subassembly and a terminal-lead-side subassembly.

The above object of the invention has been achieved, in a first aspect (1), by providing a gas sensor comprising a metal housing; a detection element fixedly disposed inside the metal housing; a terminal lead electrically connected to an electrode of the detection element; an insulating separator including an insertion hole which has a first wall surface having a first projection and a second wall surface opposite the first wall surface, and a lead wire connected with the terminal lead in the insertion hole of the separator. The terminal lead comprises a leading end connecting portion connected to the electrode of the detection element, a trailing end connecting portion connected to the lead wire, and an intermediate portion provided between the leading end connecting portion and a trailing end connecting portion. Furthermore, the intermediate portion comprises an engagement portion pressing against the first projection of the first wall and a spring tab projecting from the engagement portion and pressing against the second wall.

In a second aspect (2), the present invention provides a gas sensor according to (1) above, wherein the first projection is in fact-to-face contact with the engagement portion of the terminal lead.

In a third aspect (3), the present invention provides a gas sensor according to (1) or (2) above, wherein the separator includes a pair of second projections, and the spring tab presses against the second wall surface between the pair of second projections.

In a fourth aspect (4) of the invention according to any one of (1) to (3) above, the spring tab outwardly projects from the engagement portion in a radial direction of the separator.

EFFECTS OF THE INVENTION

Unlike a conventional sensor, the sensor of the present invention is configured such that a first projection is formed on a first wall surface of each insertion hole of the separator, and the first projection is capable of engaging and supporting a first face of the engagement portion opposite the second face, on opposing lateral sides of the spring tab. The first face of the engagement portion presses against the first projection on opposing lateral sides of the spring tab.

That is, in the present invention, the first face of the engagement portion, rather than the corners of the engagement portion, is brought into contact with, and pressed against the first wall surface of the insertion hole. Therefore, support of the engagement portion within that hole is stable as compared with a conventional support structure, and thus the leading end connecting portions of the terminal leads can be positioned in a stable manner at the front end of the separator. Therefore, in the case of the sensor of the present invention, when the terminal leads are inserted into the holes of the separator in the course of assembly thereof, the leading end connecting portions of the terminal leads can be easily disposed or positioned at the desired positions in relation to the front end surface of the separator, and the possibility of a positional shift occurring after the positioning can be reduced. Thus, in the case where the sensor of the present invention is assembled after individual assembly of an element-side subassembly and a terminal-lead-side subassembly as described above, the leading end connecting portions of the terminal leads can be smoothly fitted to a rear end portion of the element, whereby production yield can be improved.

In the invention described in (1) above, the first projection need only engage and support the first face of the engagement portion on opposing lateral sides of the spring tab. Therefore, the first projection may be formed so as to engage and support the first face at lateral end portions thereof remote from the spring tab, although the first projection may be formed so as to engage and support the first face in areas located on opposing lateral sides of the spring tab over the entire width of the engagement portion. That is, the first projection need not necessarily engage and support the lateral end corners of the engagement portion, so long as the first projection engages and supports the above-described first face. Accordingly, the first projection need not necessarily be in the form of a flat surface; however, it is preferably in face-to-face or interfacial contact with the engagement portion as described in (2) above, from the viewpoint of producing the separator. Further, the separator preferably includes a pair of second projections. The spring tab presses against the second wall surface of the separator as described in (3) above, and the positions of the terminal leads can be further stabilized by the second projections.

BRIEF DESCRIPTION OF THE DRAWINGS

FIGS. 2A and 2B are views illustrating a terminal lead (terminal lead for inner surface) for use in the gas sensor of FIG. 1, wherein FIG. 2A is a perspective view of its entirety, and FIG. 2B is a perspective view of an intermediate portion shown in FIG. 2A, as viewed from the back surface side thereof.

FIGS. 3A and 3B are views illustrating a terminal lead (terminal lead for outer surface) for use in the gas sensor of FIG. 1, wherein FIG. 3A is a perspective view of its entirety, and FIG. 3B is a perspective view of an intermediate portion shown in FIG. 3A, as viewed from the back surface side thereof.

FIGS. 4A to 4D are views illustrating a separator for use in the gas sensor of FIG. 1, wherein FIG. 4A is a cutaway front view of the separator, FIG. 4B is a central vertical sectional view of the separator of FIG. 4A, FIG. 4C is a plan view of the separator of FIG. 4A, and FIG. 4D is a sectional view of the separator of FIG. 4A taken along the line D-D of FIG. 4A.

DESCRIPTION OF REFERENCE NUMERALS

Figure 1:
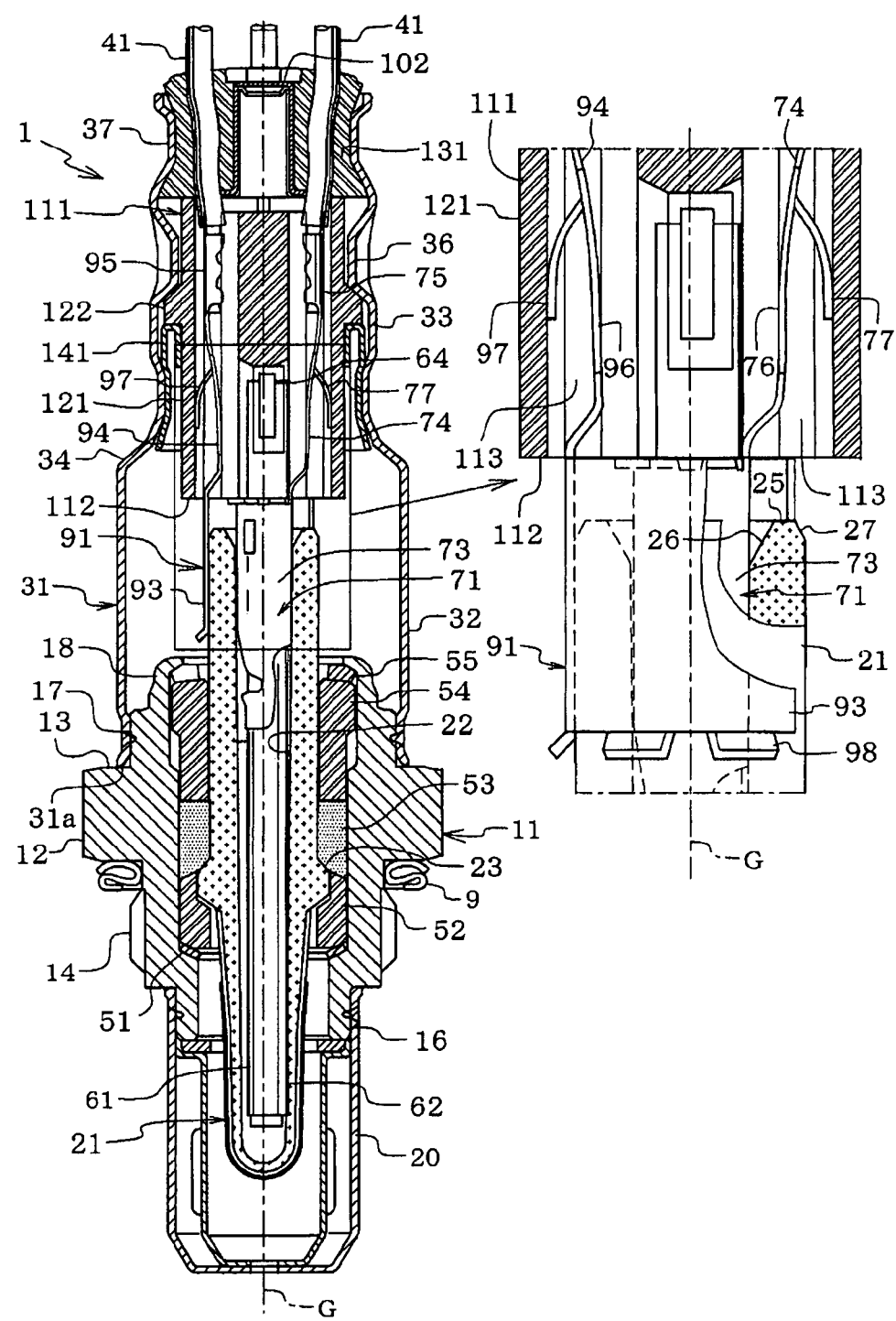
FIG. 1 is a front vertical sectional view and main-portion enlarged view illustrating a preferred embodiment of the gas sensor of the present invention.

Reference numerals used to identify various structural features in the drawings include the following.
1: gas sensor
11: metal housing
21: detection element
25: rear end of the detection element
71, 91: terminal lead
73, 93: leading end connecting portion
74, 94: intermediate portion
75, 95: trailing end connecting portion
76, 96: engagement portion of the intermediate portion
76a, 96a: second face of the engagement portion
76b, 96b: first face of the engagement portion
77, 97: spring tab
111: separator
113: insertion hole
116: groove
117: groove bottom (second wall surface)
118: first projection (first wall surface)
119: side wall
120: second projection
G: axis

DETAILED DESCRIPTION OF THE PREFERRED EMBODIMENTS

The gas sensor of the present invention will next be described in detail with reference to FIGS. 1 to 9. In the present mode, the invention is embodied as an oxygen sensor for detecting oxygen concentration in exhaust gas. Thus, the overall configuration of the sensor will first be described in detail. An oxygen sensor 1 includes a metal housing 11 in the form of a stepped cylindrical tube. A tubular sensor element 21 (in the form of a hollow cylindrical shaft) is airtightly fixed in the interior of the metal housing 11. The sensor element 21 has electrodes (electrode layers) (not shown) on inner and outer wall surfaces thereof, and has a closed front end. The element 21 has, at its intermediate portion, a large diameter portion 23 having a larger outer diameter. The front end of the element 21 projects from the front end of the metal housing 11. The element 21 is airtightly fixed in the interior of the metal housing 11 such that a ceramic holder 52 is disposed on an inner stepped portion of the metal housing 11 via a washer 51, the large diameter portion 23 of the element 21 is received, via a plate packing (not shown), in a concave portion at an inner circumferential edge of an upper end (in FIG. 1) of the ceramic holder 52, a seal material (talc) 53, a pressing ring 54, etc., are disposed, and the seal material 53 is compressed.

This fixing is performed such that a flat washer 55 is disposed in the interior of a rear end (upper end in FIG. 1) of the metal housing 11 to be located at the rear end of the pressing ring 54, and an end portion of a thin-walled tubular portion 18 at the rear end of the metal housing 11 is bent inward and crimped to compress the seal material, etc., toward the front end. Notably, the metal housing 11 has a polygonal portion 12 adapted for engaging a tool, the polygonal portion 12 being arranged on an outer circumference of an intermediate portion with respect to the vertical direction in FIG. 1. On the front end side of the polygonal portion 12, a threaded portion 14 for screwing into an exhaust pipe and a small-diameter tubular portion 16 are provided successively and integrally. A protection cover 20 with communication holes is attached to the small-diameter tubular portion 16 so as to protect the projecting front end of the element 21. Further, a thick-walled cylindrical tubular portion 17 is provided between the polygonal portion 12 and the thin-walled cylindrical tubular portion 18 at the rear end. A front-end-side large diameter portion 32 of a protection sleeve (casing) 31, the details of which will be described below, is fitted onto the thick-walled cylindrical tubular portion 17, and laser welding is performed over the entire circumference in a state where a front end surface 31a of the protection sleeve 31 is in contact with a rear-end-side flange surface 13 of the polygonal portion 12. Notably, a sealing washer 9 is fitted between the polygonal portion 12 and the threaded portion 14 of the metal housing 11. The structure having been described so far, except the protection sleeve 31 fitted and welded to the thick-walled cylindrical tubular portion 17 of the metal housing 11, corresponds to an element-side subassembly 201 shown on the left side of FIG. 5.

Notably, a hollow portion (interior) of the detection element 21 has a circular transverse cross section, and is tapped so that the diameter slightly decreases toward the front end. The centerline of the hollow portion coincides with the axis G of the metal housing 11. Further, chamfers 26 and 27 are formed at respective corners between the rear end (rear end portion) 25 of the detection element 21 and the inner and outer circumferential surfaces thereof. These chamfers 26 and 27 serve as guides when the terminal leads 71 and 91 are fitted onto and into the rear end 25, respectively, for assembly. Notably, the terminal leads 71 and 91 are identical with those described above based on FIGS. 2 and 3. In the present embodiment, a rod-shaped heater 61 having a circular cross section is inserted into the hollow portion so as to heat the detection element 21. Further, this heater 61 is passed through the interior of the tubular leading end connecting portion 73 of the terminal lead (hereinafter also referred to as the "terminal lead for inner surface") 71, which is disposed so that the terminal lead 71 is electrically connected to the electrode on the inner surface (inner wall surface) 22 of the element 21.

The tubular leading end connecting portion 73 of the terminal lead for inner surface 71 is fitted onto the electrode on the inner surface (inner side) 22 of the detection element 21 so that the leading end connecting portion 73 is pressed against and electrically connected to the electrode on the inner surface by means of a spring force of the leading end connecting portion 73. Notably, this electrode extends to the front end of the element 21 along the inner surface 22. The tubular leading end connecting portion 93 of the other terminal lead (hereinafter also referred to as the "terminal lead for outer surface") 91 is fitted onto the electrode on the outer surface (outer side) of the detection element 21 so that the leading end connecting portion 93 clamps the outer surface and is electrically connected to the electrode on the outer surface by means of a spring force of the leading end connecting portion 93. Notably, this electrode extends to the front end of the element 21 along the outer surface.

Intermediate portions 74 and 94 extend between the leading end connecting portions 73 and 93 and trailing end connecting portions 75 and 95 of the terminal leads 71 and 91; and lead wires 41 are connected to the trailing end connecting portions 75 and 95. A separator 111 formed of an electrically insulating material such as alumina is disposed rearward of the leading end connecting portions 73 and 93 of the terminal lead for inner surface 71 and the terminal lead for outer surface 91, which will be further described below. The intermediate portions 74 and 94 and distal end potions of the lead wires 41 are passed through insertion holes 113 formed in the separator 111. The distal end portions of the lead wires 41 are passed through lead-wire insertion holes formed in a cylindrical columnar seal member 131 disposed at the rear end of the oxygen sensor 1, and the lead wires 41 extend from a rear end portion of the seal member 131.

Although the details of the separator 111 will be described below, in the present embodiment, the separator 111 and the seal member 131 are both formed to have a generally cylindrical columnar shape or cylindrical shape. Each of the separator 111 and the seal member 131 has four holes which are formed at equal angular intervals about the axis G and which extend through the separator 111 in the front-rear direction (vertical direction in FIG. 1). Of the four holes of the separator 111, two opposed holes are used as the insertion holes 113, and the remaining two holes are used as holes through which a pair of lead wires 41 for supplying electricity to the heater 61 are passed. That is, the heater 61 has a heat generation portion 62 provided on one side (right side in FIG. 1) of a front end portion (lower end portion in FIG. 1) of the heater 61. The heater 61 also has a pair of terminals (only one of the terminals shown in FIG. 1) 64 provided on a side surface of a rear end portion of the heater 61 and communicating with the heat generation portion 62. The lead wires 41 are connected to the terminals 64. As in the case of the lead wires 41 connected to the terminal leads 71 and 91, the lead wires 41 connected to the terminals 64 are passed through the holes 113 of the separator 111 and the holes of the seal member 131, and extend from the rear end portion of the seal member 131. Notably, a hole 125 for receiving a rear end portion of the heater 61 is formed at the front end surface (lower surface) 112 of the separator 111, and the rear end surface of the heater 61 is in contact with the bottom of the receiving hole.

The separator 111 and the seal member 131 are covered with the protection sleeve 31 assuming the form of a stepped cylindrical tube. As described above, the front end portion of the protection sleeve 31 is fitted onto the thick-walled cylindrical tubular portion 17 of the metal housing 11, and laser welding is performed over the entire circumference in a state where the front end surface 31a of the protection sleeve 31 is in contact with the rear-end-side flange surface 13 of the polygonal portion 12. In the present embodiment, about half of the protection sleeve 31 on the front end side (lower side in FIG. 1) is formed into the large diameter portion 32, and about half of the protection sleeve 31 on the rear end side is formed into a small diameter portion 33, which is connected to the large diameter portion 32 via a taper portion 34. A portion 37 of the small diameter portion 33 surrounding the seal member 131 is crimped so as to fix the seal member 131. Further, in the present embodiment, a fixing flange 122 projects from an outer circumferential surface 121 of the separator 111 at an intermediate position with respect to the direction of the axis G. Meanwhile, the protection sleeve 31 is formed to hold the flange 122 from the front and rear sides thereof with respect to the axial direction. However, in the present embodiment, a cylindrical tubular member 141 having an upper end portion folded inwardly is disposed inside the protection sleeve 31 so that the cylindrical tubular member 141 is in contact with a surface of the flange 122 facing the front end (lower end in FIG. 1). Further, a recess portion 36 is formed on the outer circumferential surface of the small diameter portion 33 of the protection sleeve 31 so as to restrict a surface of the flange 122 facing the rear end (upper end in FIG. 1). Further, the front end facing surface of the flange 122 is pressed rearward (upward in FIG. 1) by an unillustrated upper end portion of the cylindrical tubular member 141. The outer circumferential surface of the small diameter portion 33 of the protection sleeve 31 is crimped, while being squeezed so as to compress the cylindrical tubular member 141 in a radial direction, to thereby hold the separator 111. Reference numeral 102 in FIG. 1 denotes a water-repellent ventilation member formed into a cap-like shape. The ventilation member 102, together with a metallic pipe covered with the ventilation member 102, is disposed in the seal member 131 so that the metallic pipe penetrates through the seal member 131, whereby air is introduced to the interior of the element 21.

Next, of the components of the oxygen sensor 1 of the present embodiment having the above-described structure, the details of the terminal leads (the terminal lead for inner surface 71 and the terminal lead for outer surface 91) and the separator 111, which are the features of the present invention, will be described with reference to the drawings. First, the terminal leads 71 and 91 will be described. Although these components have already been described, these components will be described more specifically (see FIGS. 1, 2, and 3 in particular). Notably, in the present embodiment, each of these components is formed by bending a thin metal plate (anti-corrosion, heat resisting supper alloy plate) punched into a predetermined shape.

Figure 2A:
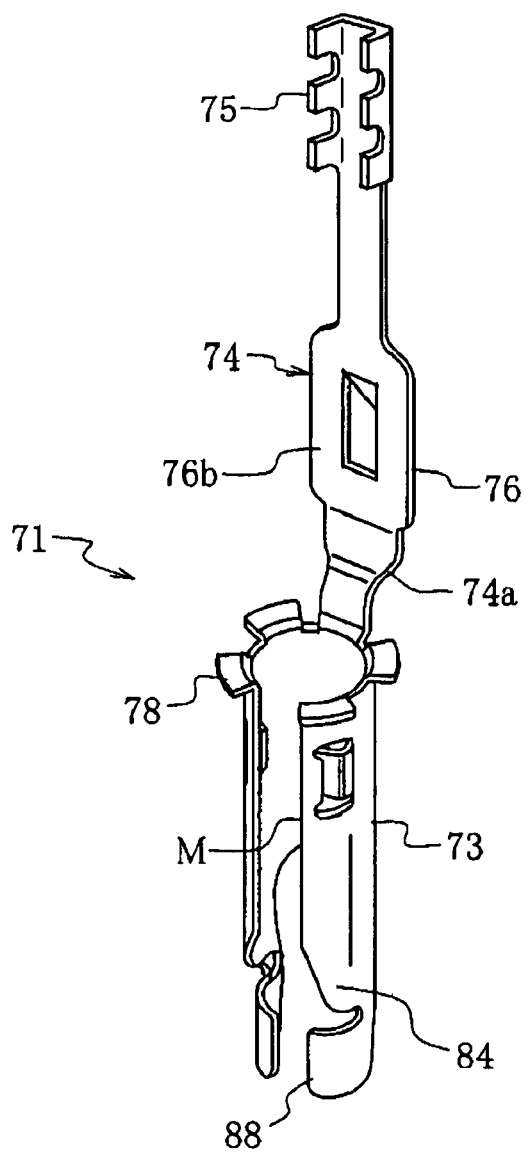
Figure 2B:
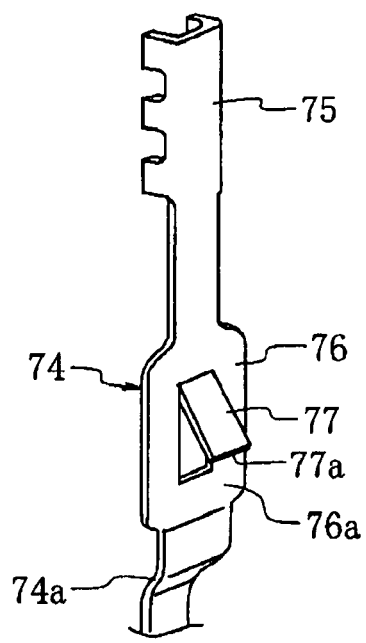

The terminal lead for inner surface 71 has, at its front end, a cylindrical tubular leading end connecting portion 73, which is disposed in the hollow portion of the rear end portion of the detection element 21 and which is pressed against and electrically connected to the electrode on the inner circumferential surface of the detection element 21. The leading end connecting portion 73 has, at one side, a slit M extending along the generating line. Therefore, when the leading end connecting portion 73 is cut along a plane (transverse cross section) perpendicular to the axis G, it has a generally C-like shape as described above. Notably, the outer diameter of the leading end connecting portion 73 in a free state is slightly greater than the inner diameter of the detection element 21, so that when the leading end connecting portion 73 is press-fitted into the hollow portion, the leading end connecting portion 73 is pressed against the electrode on the inner circumferential surface of the detection element 21 by means of the spring force of the leading end connecting portion 73. As shown in FIG. 2, an intermediate portion 74 extends upward from the rear end (upper end in FIG. 2) of the leading end connecting portion 73 at a location opposite the opening M with respect to the axis G, via an outwardly inclined bent portion 74a, so that the intermediate portion 74 slightly inclines in an outward direction. A trailing end connecting portion (connector portion) 75 with claws is provided at the upper end of the intermediate portion 74. The trailing end connecting portion 75 holds an end portion of a conductor of the lead wire 41, by means of crimping, for establishing electrical connection. Further, an engagement portion 76 wider than the remaining portion is provided on the intermediate portion 74 at a longitudinal intermediate portion thereof. A tongue-shaped spring tab 77 is formed on the engagement portion 76 at a widthwise intermediate portion thereof. The spring tab 77 is formed through punching and bending so that the spring tab 77 has an end portion 77a at its distal end thereof, and, in a free state, obliquely projects from a second face 76a of the engagement portion 76 toward the outside of the leading end connecting portion 73.

Although a detailed description will be provided below, when the leading end connecting portion 73 of the terminal lead for inner surface 71 is disposed on the front end surface 112 of the separator 111 generally concentrically with the center thereof, and the intermediate portion 74 is inserted into the insertion hole 113 of the separator 111 and pulled out to the rear end side, the spring tab 77 is pressed against the wall surface of the insertion hole 113 by means of the spring force of the spring tab 77. Meanwhile, a plurality of outwardly projecting teeth 78 are provided at the rear end (upper end in FIG. 2) of the leading end connecting portion 73. When the intermediate portion 74 is inserted into the insertion hole 113 of the separator 111 and pulled out to the rear end side, the projecting teeth 78 come into contact and engagement with the front end surface 112 of the separator 111.

In the terminal lead for inner surface 71 of the present embodiment, as shown in FIG. 2, a taper portion 84 is provided at a lower end portion of the leading end connecting portion 73. The taper portion 84 is tapered so that the diameter at its distal end is smaller than the inner diameter of the element 21, and the taper portion 84 serves as a guide when the leading end connecting portion 73 is press-fitted into the hollow portion of the element 21. Heater press portions (press portions) 88 are integrally provided below the taper portion 84 to be located on opposite sides of the slit-shaped opening M so as to press a side (left side in FIG. 1) portion of the inserted heater 61 toward one side (right side in FIG. 1) of the wall surface 22 of the hollow portion of the element 21.

Next, the terminal lead for outer surface 91 will be described in detail with reference to FIG. 3A, etc. As described above, this terminal lead for outer surface 91 has, at its front end, a cylindrical tubular leading end connecting portion 93, which is pressed against and electrically connected to the electrode on the outer circumferential surface of the rear end portion of the detection element 21. The leading end connecting portion 93 has, at one side, a slit M extending along the generating line. Therefore, when the leading end connecting portion 93 is cut along a plane (transverse cross section) perpendicular to the axis G, it has a generally C-like shape as described above. Notably, the outer diameter of the leading end connecting portion 93 in a free state is slightly smaller than the outer diameter of the detection element 21, so that when the leading end connecting portion 93 is press-fitted onto the rear end portion of the element 21, the leading end connecting portion 93 is pressed against the electrode by means of the spring force of the leading end connecting portion 93. Further, a plurality of teeth 98 which project in an outwardly expanding fashion are provided at the front end (lower end in FIG. 3A) of the leading end connecting portion 93 to serve as a guide when the leading end connecting portion 93 is press-fitted on the rear end portion of the element 21.

Figure 3A:
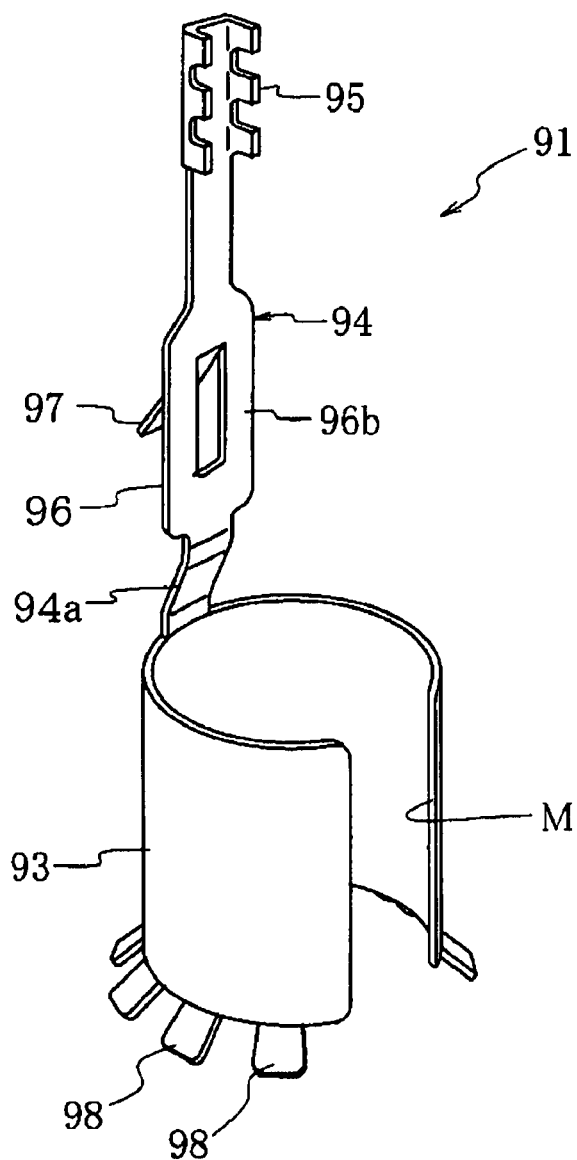
Figure 3B:
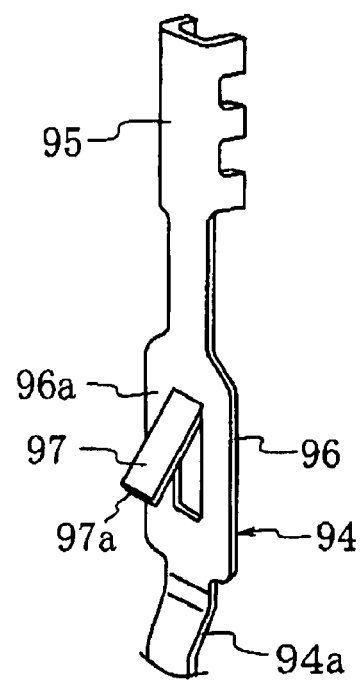
Figure 4A:
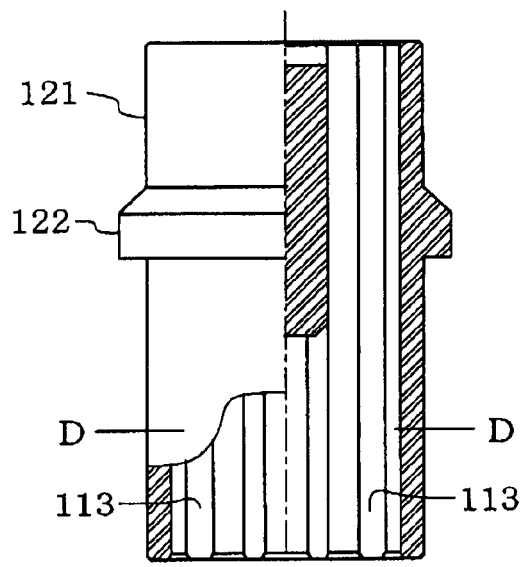
Figure 4B:
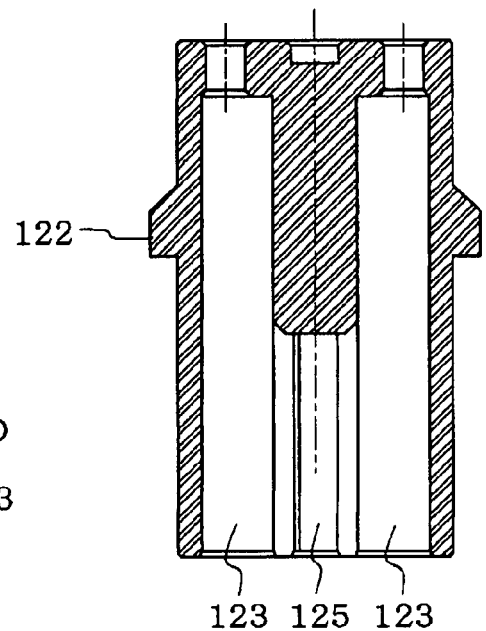
Figure 4C:
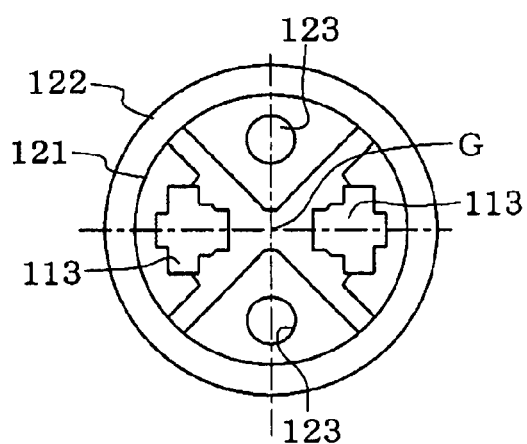
Figure 4D:
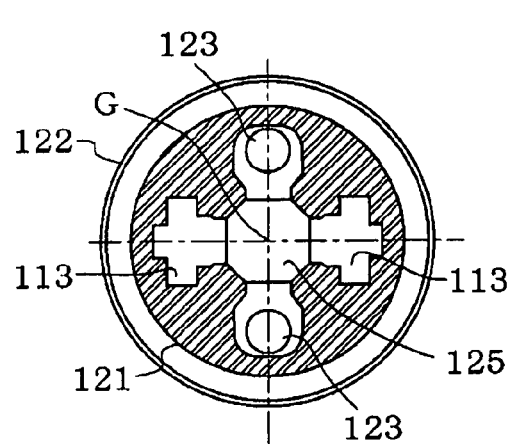

As shown in FIG. 3A, an intermediate portion 94 extends upward from the rear end (upper end in FIG. 3A) of the leading end connecting portion 93 at a location opposite the opening M with respect to the axis G, via an inwardly inclined bent portion 94a, so that the intermediate portion 94 slightly inclines in an outward direction. A trailing end connecting portion (connector portion) 95 with claws is provided at the upper end of the intermediate portion 94. The trailing end connecting portion 95 holds an end portion of a conductor of the lead wire 41, by means of crimping, for establishing electrical connection. Further, between the leading end connecting portion 93 and the trailing end connecting portion (connector portion) 95, the intermediate portion 94 has an engagement portion 96 wider than the trailing end connecting portion 95. A tongue-shaped spring tab 97 is formed on the engagement portion 96 at a widthwise intermediate portion thereof. The spring tab 97 is formed through punching and bending so that the spring tab 97 has an end portion 97a at its distal end thereof, and, in a free state, obliquely projects from a second face 96a of the engagement portion 96. Notably, although the terminal leads 71 and 91 differ in the shapes and dimensions of the leading end connecting portions 73 and 93 and portions located forward thereof, the terminal leads 71 and 91 are the same in terms of the shapes and dimensions of the remaining portions (the intermediate portions 74 and 94, etc.), except for the bent portions 74a and 94a.

When the leading end connecting portion 93 of the terminal lead for inner surface 91 is disposed on the front end surface 112 of the separator 111 generally concentrically with the center thereof, and the intermediate portion 94 is inserted into the insertion hole 113 of the separator 111 and pulled out to the rear end side, the spring tab 97 is pressed against the wall surface of the insertion hole 113 by means of the spring force of the spring tab 97. When the intermediate portion 94 is inserted into the insertion hole 113 of the separator 111 and pulled out to the rear end side, the rear end (upper end in FIG. 1) of the leading end connecting portion 93 comes into contact with the front end surface 112 of the separator 111.

Figure 9:
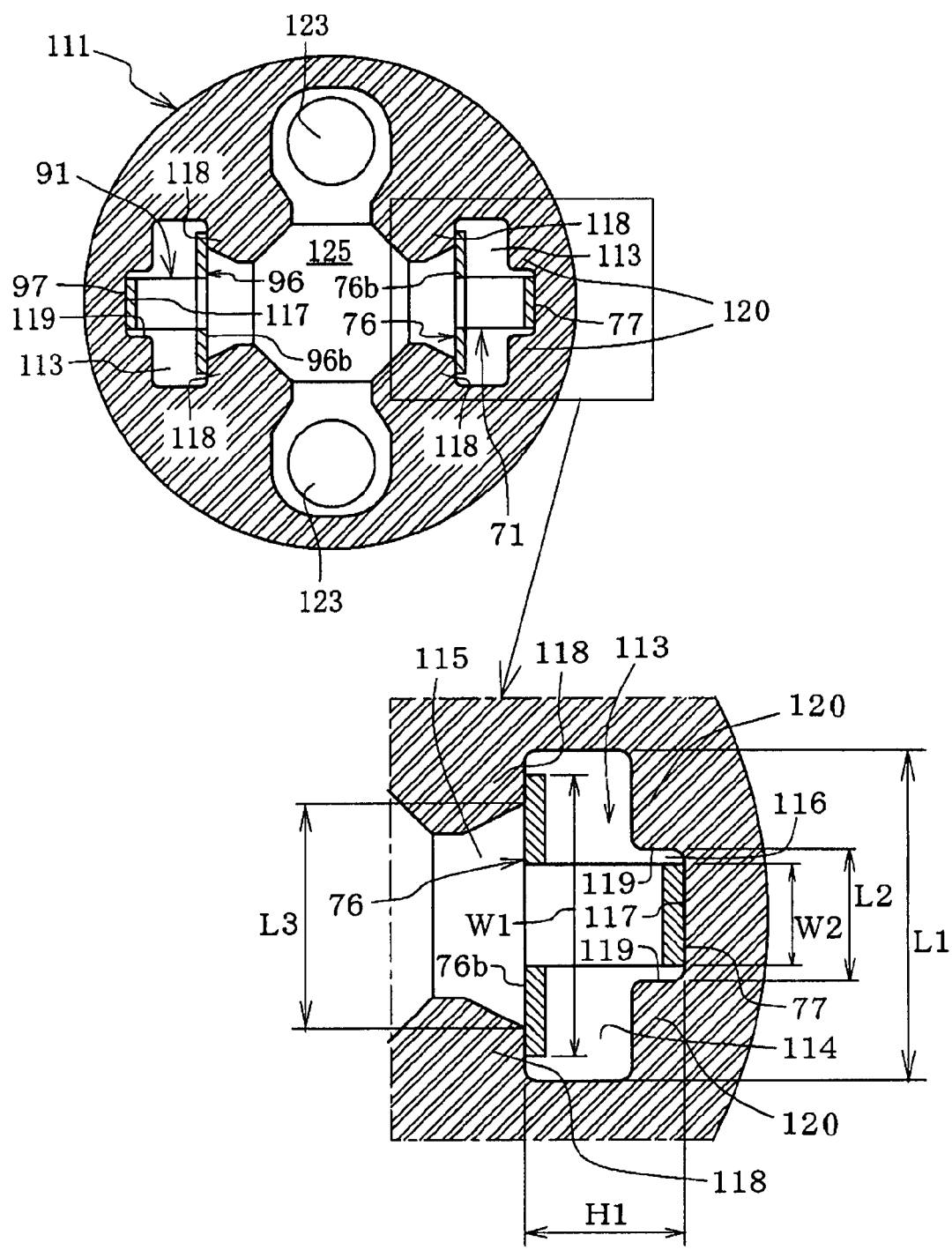
FIG. 9 is a sectional view of the terminal-lead-side subassembly on the right side of FIG. 5 taken along the line B-B and its main-portion enlarged view.

Next, the separator 111 of the present embodiment will be described in detail with reference to FIGS. 4A to 4D. As described above, the separator 111 assumes a cylindrical columnar shape, and the flange 122, which extends in the circumferential direction, projects from the outer circumferential surface 121 of the separator 111 at an intermediate position with respect to the front-rear direction (vertical direction in FIG. 4). The separator 111 has four holes which are formed at equal angular intervals around the axis G and which extend through the separator 111 in the front-rear direction. Of the four holes, two opposed holes are used as holes 113 for the terminal leads 71 and 91 connected to the electrodes of the element 21, and the remaining two holes are used as holes 123 for inserting the pair of lead wires 41 for supplying electricity to the heater. The holes 113 and the holes 123 are disposed symmetrically with respect to the axis G. As shown in FIG. 9, each of the insertion holes 113 is formed by a rectangular hole 114, which is elongated in a direction tangent to the outer circumference in its transverse cross section. A groove 115 which is concaved inward or toward the axis G and a groove 116 which is concaved outward or in the direction opposite the axis G are formed at the centers of the respective longer sides of the rectangular hole 114 such that the grooves 115 and 116 extend along the axis G.

In the transverse cross section, each longer side of the rectangular hole 114 has a length L1 slightly greater than the width W1 of the engagement portion 76, 96 of the above-described terminal lead 71, 91. The width L2 of the groove (hereinafter also referred to as "outside groove") 116 which is located at the center of one longer side of the rectangular hole 114 and which is concaved outward is slightly greater than the width W2 of the spring tab 77, 97 of the terminal lead 71, 91. As described below, the end portion (distal end portion) 77a, 97a of the spring tab 77, 97 is pressed against a groove bottom 117, which is the second wall surface. Meanwhile, the width of the groove 115 which is located at the center of the other longer side of the rectangular hole 114 and which is concaved inward decreases toward the axis G in the transverse cross section. However, the groove width L3 as measured at a portion along the other longer side of the rectangular hole 114 is smaller than the width W1 of the engagement portion 76, 96. Thus, ledge-shaped first projections 118, each forming a flat surface, are provided on the wall surface of the rectangular hole 114 to be located on opposing lateral sides of the groove 115 so that the first projections 118 are located opposite the groove bottom 117. Notably, the insertion holes 113 have a constant transverse cross sectional shape as described above, and extend through the separator 111 in the front-rear direction. The dimension H1 from the ledge-shaped first projections 118 to the groove bottom 117 of the groove 116, which is concaved outwardly; i.e., the sum of the length of the shorter sides of the rectangular hole 114 and the depth of the groove 116, is set to be smaller than the projection amounts T1 and T2 (see FIG. 6) of the spring tabs 77 and 97 of the engagement portions 76 and 96 of the terminal leads 71 and 91.

The terminal leads 71 and 91 are inserted, from their trailing end connecting portions 75 and 95, into the insertion holes 113, which have the above-described transverse cross section, from the side where the front end surface 112 of the separator 111 is present, in such a manner that the spring tabs 77 and 97 pass through the outside grooves 116, and the engagement portions 76 and 96 of the intermediate portions 74 and 94 pass through the rectangular holes 114. Subsequently, the lead wires 41 connected to the trailing end connecting portions 75 and 95 are pulled from the rear end side of the separator 111, whereby the distal end portions of the spring tabs 77 and 97 are pressed against the groove bottoms 117 of the outer groves 116 by means of the spring (plate spring) forces of the spring tabs 77 and 97. Simultaneously, the first faces 76b and 96b of the engagement portions 76 and 96 are positioned, while being pressed against the first projections 118 at the opposing lateral sides of the engagement portions. Notably, in the present embodiment, the first faces 76b and 96b are pressed against the first projections 118 in limited areas extending in the front-rear direction of the engagement portions 76 and 96; i.e., areas corresponding to the front end portions of the spring tabs 77 and 97. Notably, in the present embodiment, side walls 119 rising from the groove bottom 117 of each outside groove 116 restrict motion of the engagement portion 76, 96 in the widthwise direction.

Referring back to FIG. 4, the oxygen sensor 1 of the present embodiment is provided with a heater. Although the holes 123, through which the lead wires 41 for the heater are passed, are also formed in the separator 111, these holes 123 each have a circular transverse cross section. Notably, rear end portions of the holes 123 each have a reduced inner diameter. Further, in the present embodiment, the hole 125 for receiving the rear end portion of the heater 61 is formed at the center of the front end surface (lower surface) 112 of the separator 111 as described above, and the hole 125 removes axis-G-side portions of the walls of the above-described four holes 113 and 123, and communicates therewith. Thus, when the separator 111 is viewed from the front end side (lower side in FIG. 1), the holes 113 and 123 form a cruciform space extending from the hole 125 for the heater (see FIG. 4D). This is because if a wall is provided between the central hole 125 for the heater and the other holes 113 and 123 around the hole 125, the wall becomes thin and the structure becomes complex. Also, when the terminal lead for inner surface 71 is inserted into the corresponding hole 113, the bent portion 74a adjacent to the leading end connecting portion 73 interferes with the wall. Accordingly, in the case where such a problem does not occur, the axis-G-side groove 115 may be omitted.

Figure 5:
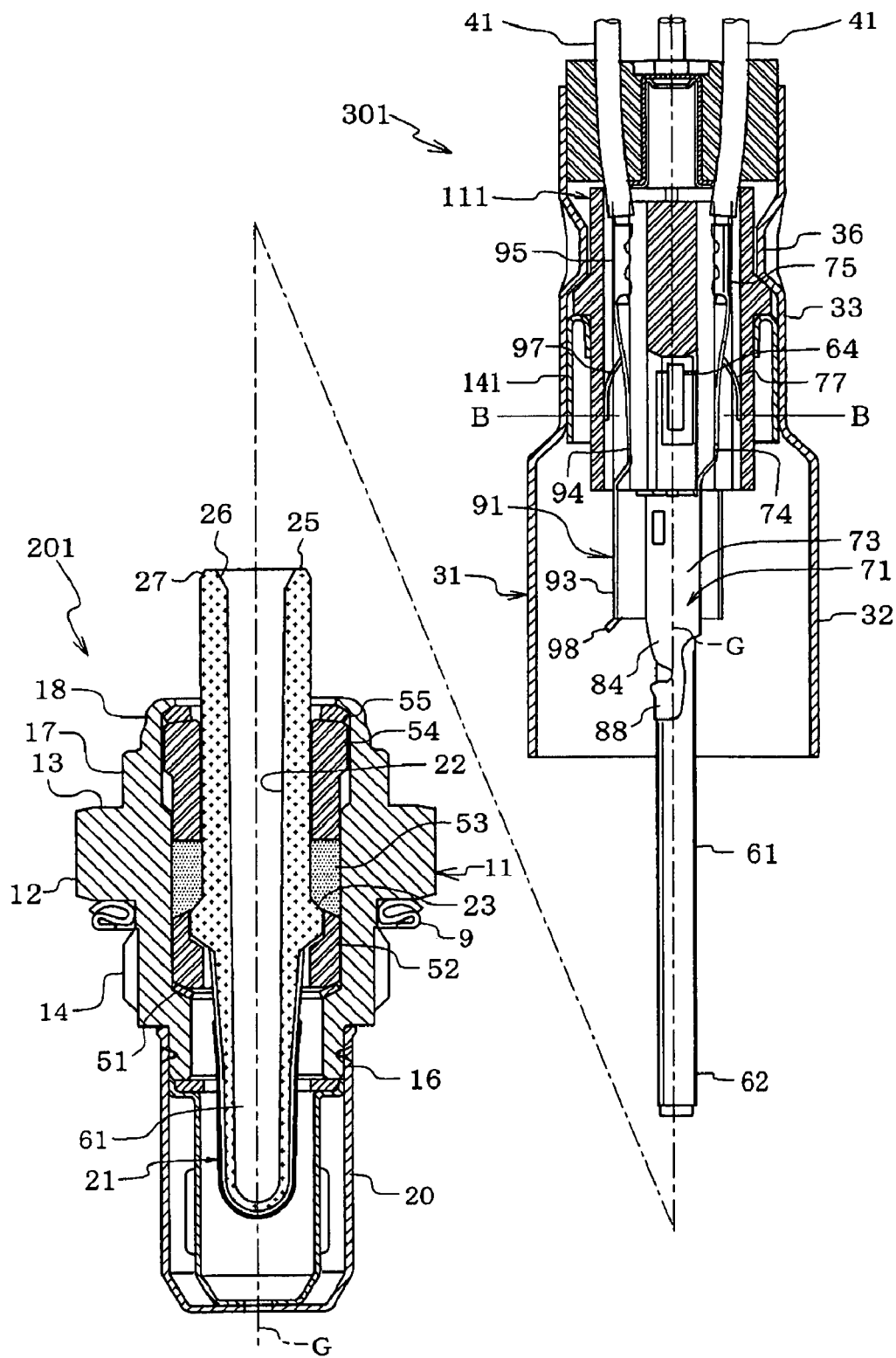
FIG. 5 is a sectional view illustrating the step of assembling the gas sensor of FIG. 1.
Figure 6:
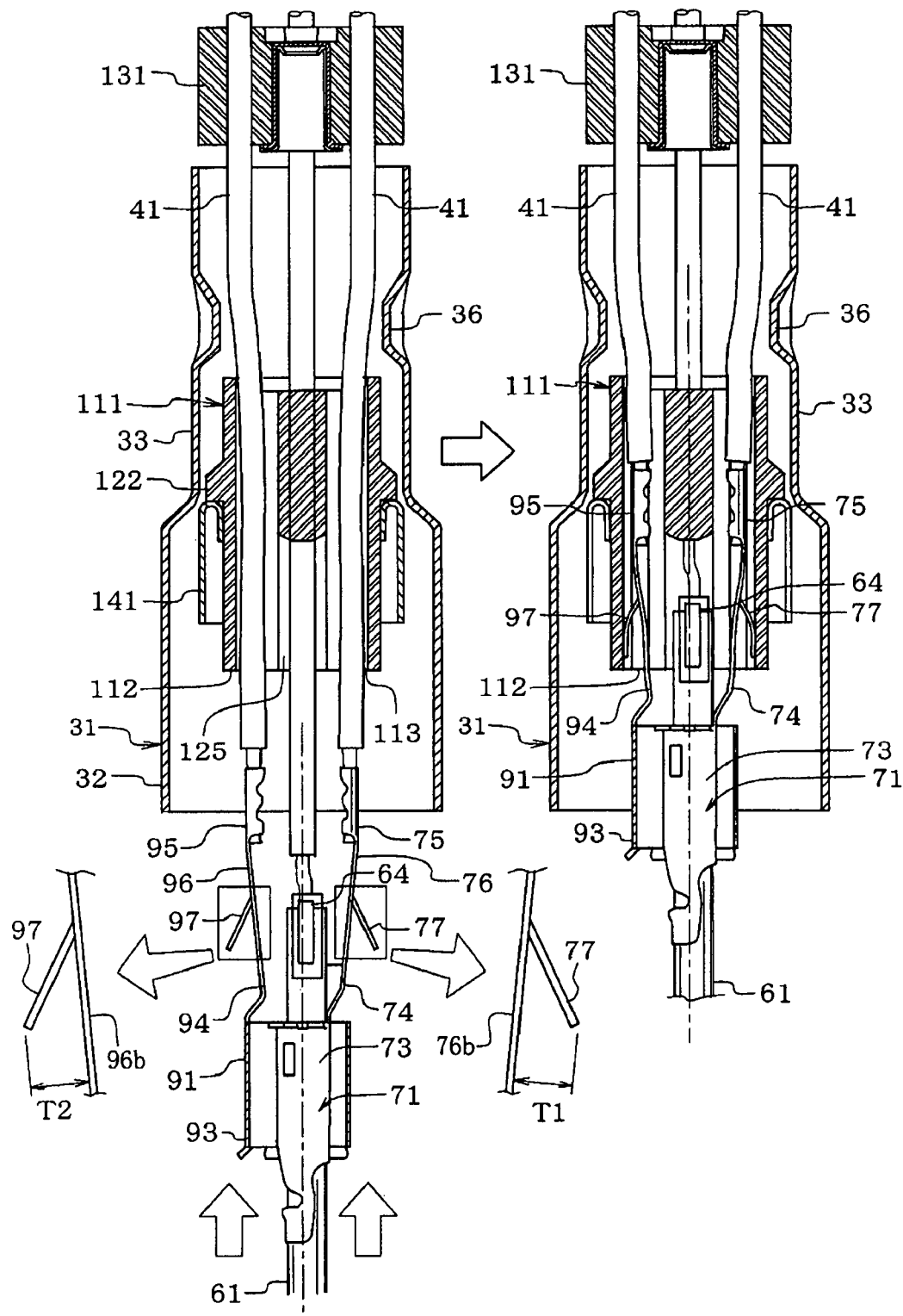
FIG. 6 is an explanatory view showing assembly of a terminal-lead-side subassembly of FIG. 5.
Figure 7:
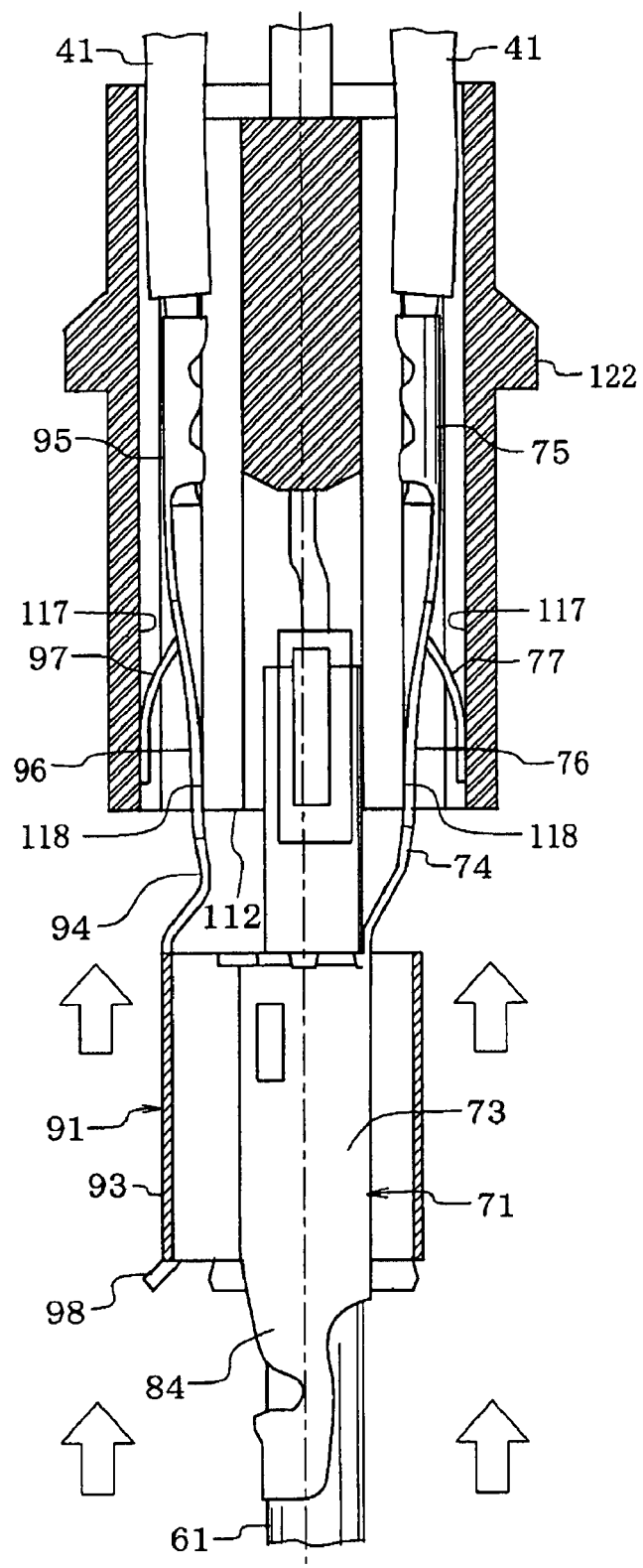
FIG. 7 is a main-portion enlarged view of the right-side drawing of FIG. 6.
Figure 8:
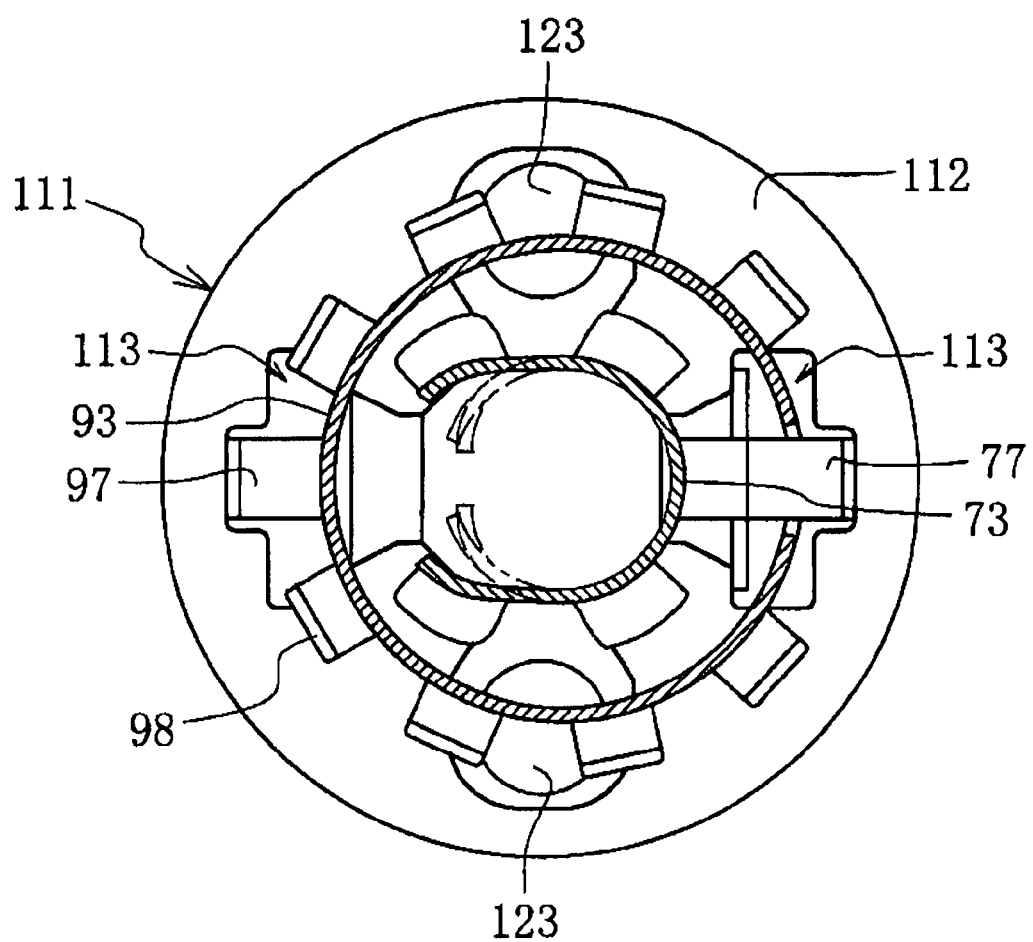
FIG. 8 is a view illustrating the positional relation between the front end surface of the separator and the leading end connecting portions when the terminal-lead-side subassembly on the right side of FIG. 5 is viewed from the front end side.

As preparation for assembling the oxygen sensor 1 of the present embodiment, the terminal-lead-side subassembly 301 shown on the right side of FIG. 5 is assembled separately from the element-side subassembly 201 shown on the left side of FIG. 5 which includes the element 21 fixed to the metal housing 11. The terminal-lead-side subassembly 301 is assembled as shown in FIG. 6. Specifically, the lead wires 41 are passed through the seal member 131 and then through the holes of the separator 111 from the rear end side. Of the distal ends of these lead wires, the distal ends of two lead wires are connected to the trailing end connecting portions 75 and 95 of the terminal leads 71 and 91, and the distal ends of the remaining two lead wires are connected to the terminals 64 at the rear end of the heater 61. Notably, before this connection, the protection sleeve 31 is fitted on the separator 111 in advance. The lead wires 41 are pulled toward the rear end side in such a manner that the leading end connecting portions 73 and 93 of the terminal leads 71 and 91 are held at a predetermined position (at the center in the present embodiment) of the front end surface 112 of the separator 111, and the trailing end connecting portions 75 and 95 and the intermediate portions 74 and 94 are received in the insertion holes 113 of the separator 111 (see FIG. 7). Notably, this pulling operation is performed in such a manner that the engagement portions 76 and 96 of the terminal leads 71 and 91 pass through the rectangular holes 114, the spring tabs 77 and 97 thereof pass through the outer groves 116, and the rear end portion of the heater 61 enters the hole 125 at the center of the front end surface 112 of the separator 111. After the lead wires 41 are pulled toward the rear end side, the protection sleeve 31 is fitted onto the separator 111, and the seal member 131 is press fitted into the interior of a rear end portion of the protection sleeve 31. Thus, the terminal-lead-side subassembly 301 shown on the right side of FIG. 5 is completed. Notably, before the protection sleeve 31 is fitted, the cylindrical tubular member 141 is fitted onto the outer circumference of the separator 111 from its front end side so that the cylindrical tubular member 141 comes into contact with the front-end-facing surface of the flange 122 of the separator 111.

In this assembly, within the insertion hole 113, the spring tab 77, 97 of the terminal lead 71, 91 is pressed against the groove bottom 117 of the outside groove 116 by means of the spring (plate spring) force of the spring tab 77, 97. Meanwhile, the first face 76b, 96b of the engagement portion 76, 96 is pressed against and in face-to-face contact with the flat, ledge-shaped first projections 118 at the opposite lateral sides of the engagement portion 76, 96 in the present embodiment. Thus, the invention differs from the conventional technique in which the corners between the second face and the lateral side surfaces come into contact with and are supported by the inclined wall surfaces of a generally triangular hole. The leading end connecting portion 73, 93 is disposed at a predetermined position (concentric with the center in the present embodiment) of the front end surface 112 of the separator 111 with the rear end of the leading end connecting portion 73, 93 brought into contact with the front end surface 112 (see FIG. 8).

In such assembly, in the present embodiment, the terminal lead 71, 91 is pulled in such a manner that, within the insertion hole 113, the spring tab 77, 97 is pressed against the groove bottom 117 of the outside groove 116, and simultaneously, the first face 76b, 96b of the engagement portion 76, 96 is pressed against and in face-to-face contact with the flat, ledge-shaped first projections 118 in the areas on opposing lateral (left and right) sides of the spring tab 77, 97 (see FIG. 9). Therefore, the terminal lead 71, 91 does not rotate about the intermediate portion 74, 94 in the transverse cross section, including the pull-in step. Accordingly, the leading end connecting portions 73 and 93 can be disposed at desired positions of the front end surface 112 of the separator 111 easily and stably (see FIG. 4). Notably, as described above, the tapered portion 84 is provided at the front end side of the terminal lead 71, and the plurality of outwardly expanded teeth 98 are provided on the front end side of the terminal lead 91. Since the tapered portion 84 and the teeth 98 serve as guides when the leading end connecting portions 73 and 93 are fitted to the rear end portion of the detection element 21, the disposed positions may be slightly offset. Further, the positions do not change after the positioning. That is, since the present embodiment employs a structure in which the first face 76b, 96b of the engagement portion 76, 96, rather than the corners of the engagement portion 76, 96, is pressed against the first projections 118, which are portions of the wall surface of the insertion hole 113, in the course of assembling the sensor, the engagement portion 76, 96 is supported within the hole more stably as compared with a conventional support structure. Accordingly, the position of the leading end connecting portion 73, 93 of the terminal lead 71, 91 can be stabilized at the front end of the separator 111. In addition, in the present embodiment, the spring tab 77, 97 is pressed against the groove bottom 117 of the outside groove 116 within the insertion hole 113, and the spring tab 77, 97 is restricted from moving in the widthwise direction by means of the side walls 119 rising from the groove bottom 117. Therefore, yet more stable support is realized.

The thus-obtained terminal-lead-side subassembly 301 and the element-side subassembly 201 including the element 21 fixed to the metal housing 11 are positioned so that their axes G coincide with one another. Subsequently, the leading end connecting portions 73 and 93 of the terminal leads 71 and 91 are fitted to the rear end portion of the detection element 21 (see FIG. 5). Although the sensor is assembled in this manner, in the present embodiment, the leading end connecting portions 73 and 93 of the terminal leads 71 and 91 of the terminal-lead-side subassembly 301 impart no positional shift on the front end surface 112 of the separator 111. Therefore, in the course of the assembly, the leading end connecting portions 73 and 93 of the terminal leads 71 and 91 are smoothly fitted to the rear end portion of the detection element 21. Accordingly, it is possible to effectively prevent the front ends of the leading end connecting portions 73 and 93 of the terminal leads 71 and 91 from colliding with the rear end of the element 21 in the course of assembling the sensor, which collision could otherwise crush the front ends of the leading end connecting portions 73 and 93, or generate chips or cracks at the rear end portion of the element 21. It is also possible to effectively prevent the occurrence of joint failure, which could otherwise occur due to crushing, chipping, or cracking.

After the leading end connecting portions 73 and 93 are fitted to the rear end of the element 21, the outer circumference of the front end of the protection sleeve 31 is welded to the body at 17. Also, a portion of the small diameter portion 33 of the protection sleeve 31 corresponding to the cylindrical tubular member 141 and a suitable portion of the outer circumferential surface of the seal member 131 are crimped, while being squeezed, whereby the oxygen sensor 1 shown in FIG. 1 is completed.

Figure 10:
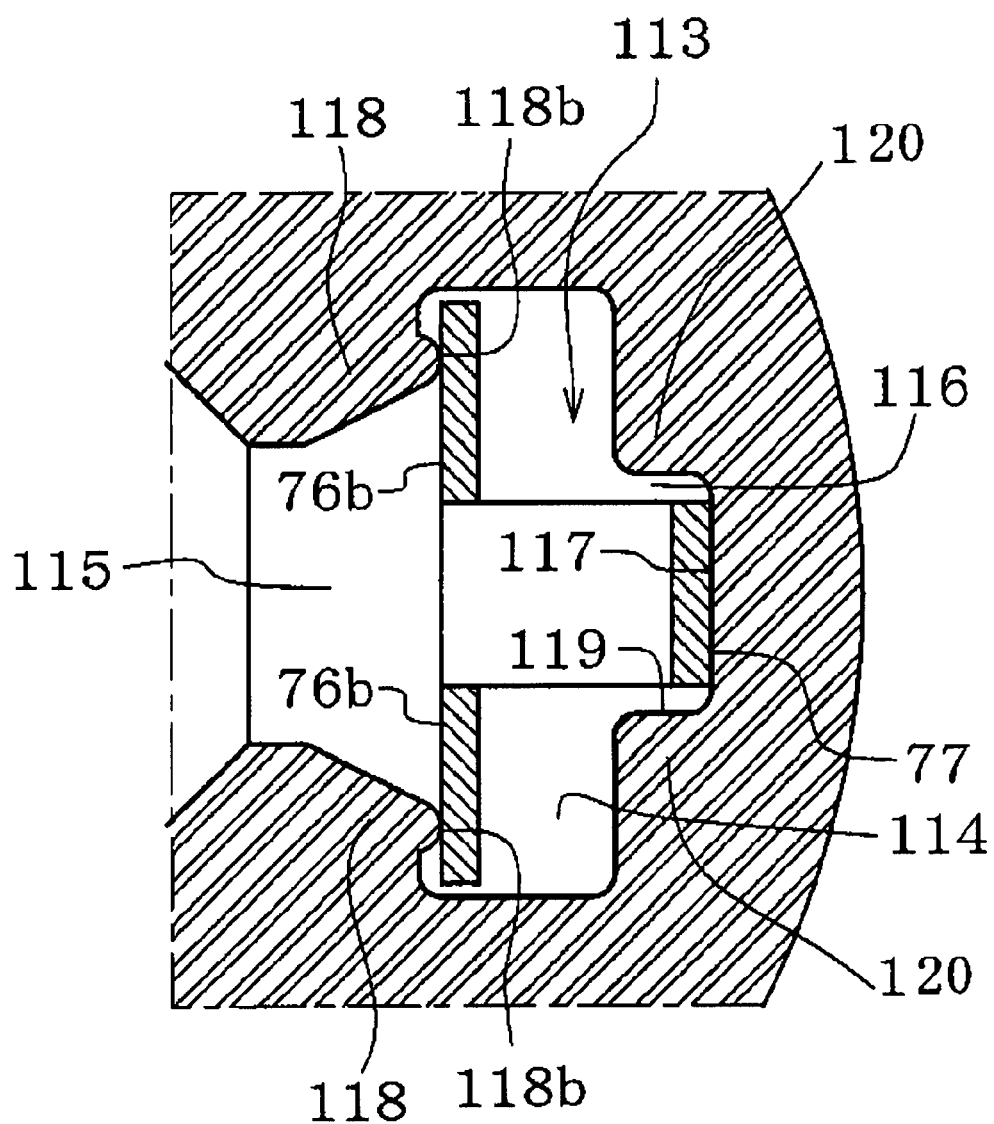
FIG. 10 is a transverse sectional view of another example of the insertion hole.
Figure 11:
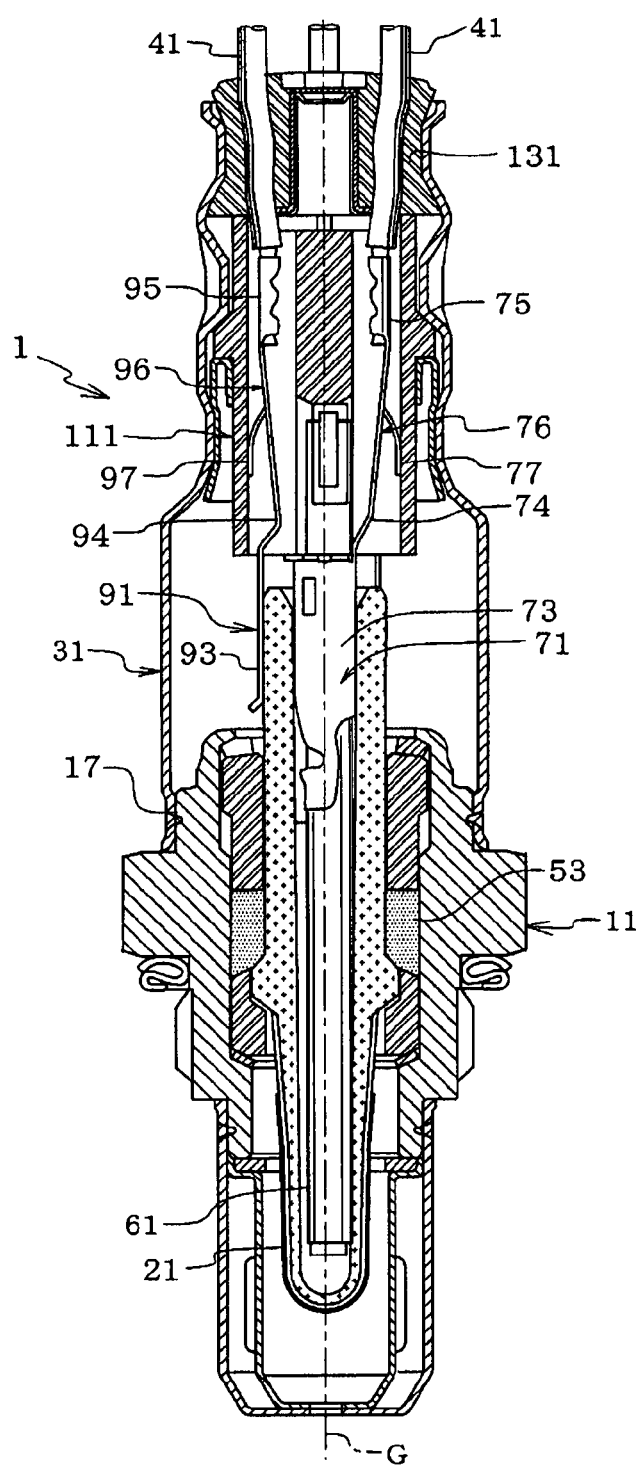
FIG. 11 is a front vertical sectional view of a conventional gas sensor.
Figure 12:
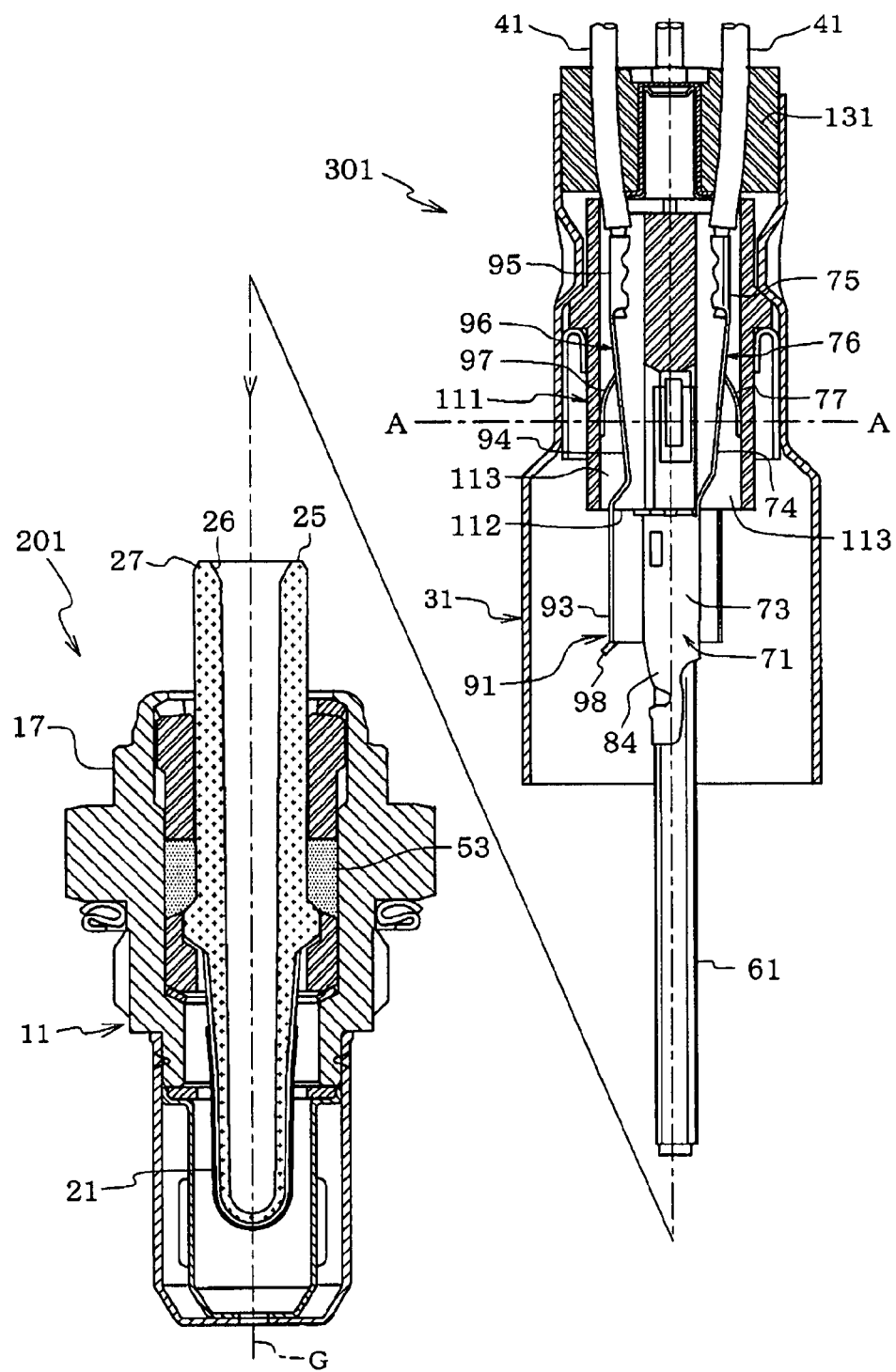
FIG. 12 is a sectional view illustrating the step of assembling the gas sensor of FIG. 11.
Figure 13:
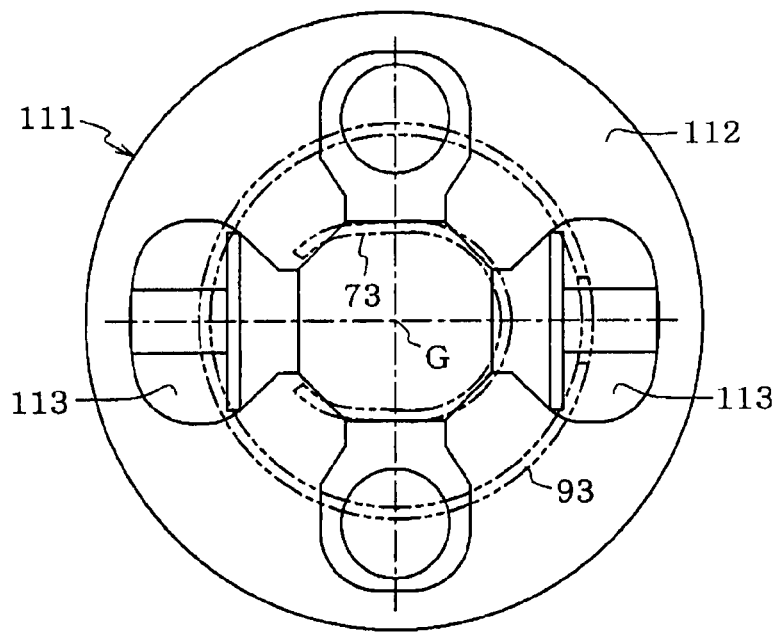
FIG. 13 is an enlarged view of the separator of the terminal-lead-side subassembly on the right side of FIG. 12 as viewed from the front end side.
Figure 14:
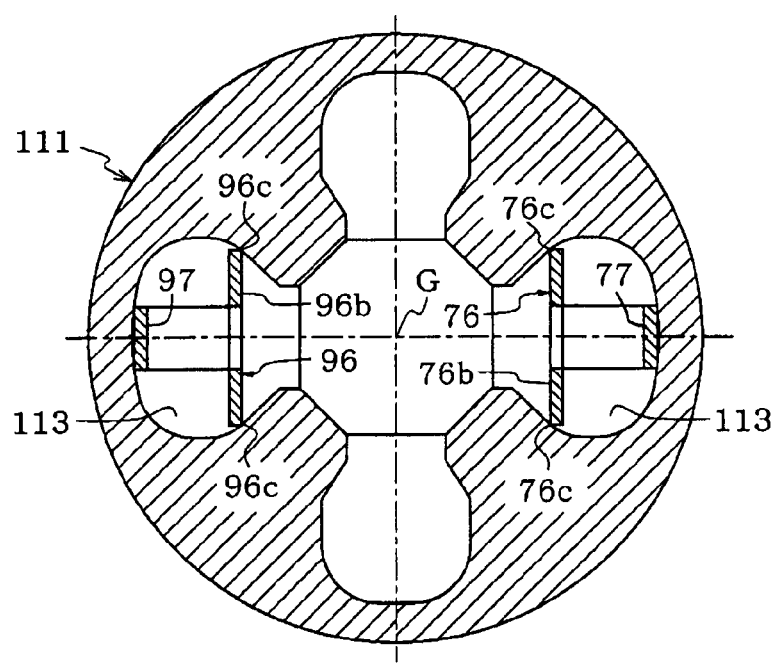
FIG. 14 is an enlarged sectional view taken along the line A-A of FIG. 12.
Figure 15:
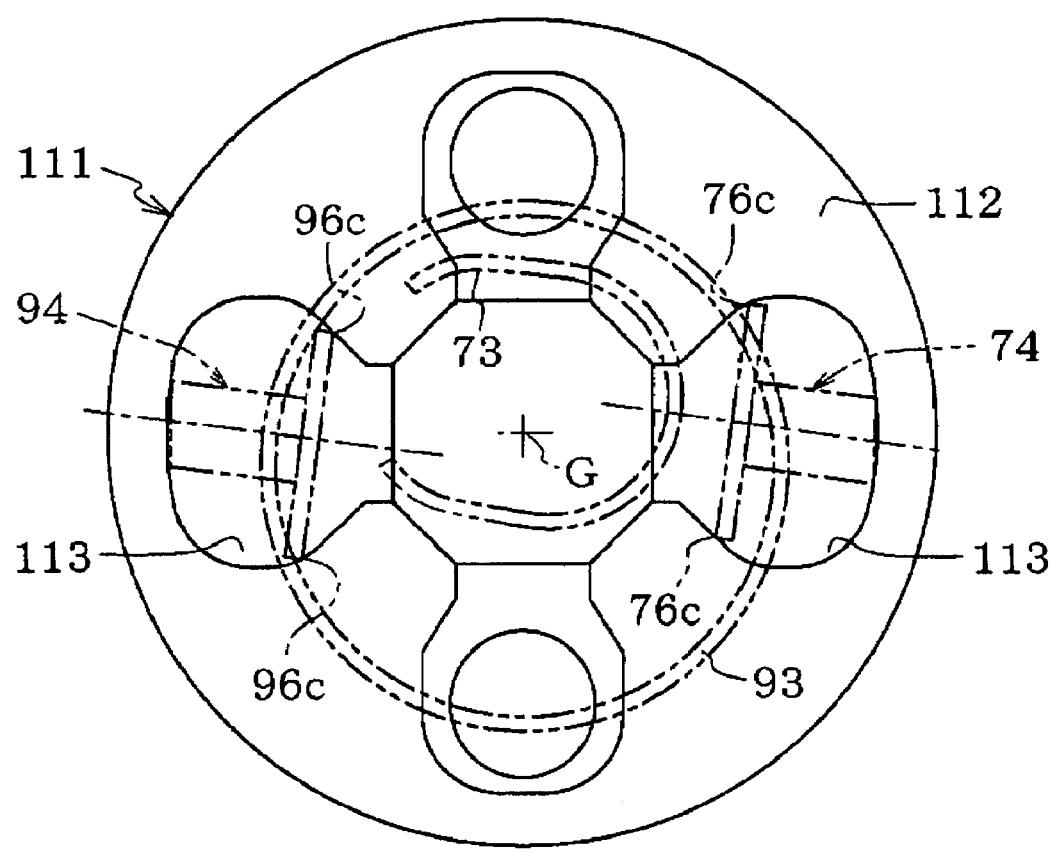
FIG. 15 is an explanatory view showing a state where the positions of the leading end connecting portions of the terminal leads have changed on the front end surface of the separator.

In the above-described oxygen sensor of the present embodiment, the ledge-shaped first projections 118 are each formed by a flat surface; however, the first projections are not necessarily flat. Rather, the first projections 118 need only support the first face 76b, 96b of the engagement portion 76, 96 in the areas located on opposing lateral sides of the spring tabs 77, 97. FIG. 10 shows a modified embodiment. In the case of the insertion hole 113 shown in FIG. 10, in a transverse cross section thereof, convex portions 118b are provided on opposite sides of the groove 115 so that the convex portions 118b can support the first face 76b, 96b of the engagement portion 76, 96 in areas located on opposing lateral sides of the spring tabs 77, 97. In this case as well, the first projections can come into contact with and support the first face, unlike the case of the conventional technique in which the lateral end corners of the engagement portion 76, 96 are supported. That is, in the present invention, a first projection is formed on a wall surface of each insertion hole opposite the wall surface against which the spring tab is pressed, and the first projection supports the first face of the engagement portion in an area located on opposing lateral sides of the spring tab. The present invention can be modified so long as the first face of the engagement portion is pressed against the first projection in an area located on opposing lateral sides of the spring tab.

Further, in the present embodiment, each insertion hole 113 has an axis-G-side groove 115 which overlaps the hole 125 for the heater as viewed from the front end side of the separator 111. However, as described above, in the case where the sensor does not include a heater, or where the terminal lead for inner surface 71 can be inserted into the hole 113 without hindrance, the groove 115 can be omitted. Accordingly, in such a case, the insertion holes 113 each assume a convex transverse cross section when the outside groove 116 is provided, or a simple rectangular transverse cross section when the outside groove 116 is not provided.

The gas sensor of the present invention is not limited to that of the above-described embodiment. The gas sensor of the present invention can be modified as appropriate in terms of structure and configuration without departing from the spirit or scope of the invention. For example, in the above-described embodiment, the present invention is embodied as a sensor equipped with a heater. However, the present invention can be embodied irrespective of whether or not a heater is provided. In the above-described embodiment, the present invention is embodied as an oxygen sensor. However, the present invention can be similarly embodied as another type of sensor.

This application is based on Japanese Patent Application No. 2006-111138 filed Apr. 13, 2006, incorporated by reference herewith in its entirety.

What is claimed is:

1. A gas sensor comprising:
a metal housing;
a detection element fixedly disposed inside the metal housing;
a terminal lead electrically connected to an electrode of the detection element;

an insulating separator including an insertion hole which has a first wall surface having a first projection and a second wall surface opposite the first wall surface, and a lead wire connected with the terminal lead in the insertion hole of the separator, wherein the terminal lead comprises:

a leading end connecting portion connected to the electrode of the detection element, a trailing end connecting portion connected to the lead wire, and an intermediate portion provided between the leading end connecting portion and a trailing end connecting portion, wherein the intermediate portion comprises:

an engagement portion pressing against the first projection of the first wall; and a spring tab projecting from the engagement portion and pressing against the second wall.

2. The gas sensor according to claim 1, wherein the first projection is in face-to-face contact with the engagement portion of the terminal lead.

3. The gas sensor according to claim 1, wherein the separator includes a pair of second projections, said spring tab pressing against the second wall surface between the pair of second projections.

4. The gas sensor according to claim 1, wherein the spring tab outwardly projects from the engagement portion in a radial direction of the separator.

5. The gas sensor according to claim 1, wherein the spring tab is formed at a widthwise intermediate portion of the engagement portion, the spring tab has a distal end portion which obliquely projects from a second face of the engagement portion so as to press against the second wall of the insertion hole, and a first face of the engagement portion on opposing lateral sides of the spring tab presses against the first projection of the first wall, whereby axial rotation of the terminal lead within the insertion hole is restricted.

* * * * *